(12) United States Patent
Hessel et al.

(10) Patent No.: US 8,937,102 B2
(45) Date of Patent: Jan. 20, 2015

(54) FLUID COCAMIDE MONOETHANOLAMIDE CONCENTRATES AND METHODS OF PREPARATION

(75) Inventors: John F. Hessel, Blue Bell, PA (US); Stephen F. Gross, Souderton, PA (US); Anna Kvecher, Chalfont, PA (US)

(73) Assignee: Cognis IP Management GmbH, Duesseldorf (DE)

( * ) Notice: Subject to any disclaimer, the term of this patent is extended or adjusted under 35 U.S.C. 154(b) by 3 days.

(21) Appl. No.: 13/634,081

(22) PCT Filed: Feb. 26, 2011

(86) PCT No.: PCT/EP2011/000948
§ 371 (c)(1),
(2), (4) Date: Sep. 11, 2012

(87) PCT Pub. No.: WO2011/110291
PCT Pub. Date: Sep. 15, 2011

(65) Prior Publication Data
US 2013/0012601 A1    Jan. 10, 2013

Related U.S. Application Data

(60) Provisional application No. 61/313,395, filed on Mar. 12, 2010.

(51) Int. Cl.
| | | |
|---|---|---|
| A61Q 19/00 | (2006.01) | |
| A61K 8/34 | (2006.01) | |
| A61K 8/42 | (2006.01) | |
| C11D 1/52 | (2006.01) | |

(52) U.S. Cl.
CPC . A61K 8/42 (2013.01); A61K 8/345 (2013.01); A61Q 19/00 (2013.01)
USPC ............................ 516/27; 510/499; 424/70.31

(58) Field of Classification Search
None
See application file for complete search history.

(56) References Cited

U.S. PATENT DOCUMENTS

| | | | | |
|---|---|---|---|---|
| 4,440,665 | A | * | 4/1984 | Mather et al. .................. 516/27 |
| 4,488,981 | A | * | 12/1984 | Urfer et al. .................... 510/405 |
| 5,719,117 | A | * | 2/1998 | Falk et al. ..................... 510/475 |
| 6,765,024 | B1 | | 7/2004 | Gray et al. |
| 2001/0044405 | A1 | | 11/2001 | Perella et al. |
| 2004/0234467 | A1 | * | 11/2004 | Ananthapadmanabhan et al. ............................ 424/70.1 |
| 2008/0139434 | A1 | * | 6/2008 | Basappa et al. ............... 510/159 |

FOREIGN PATENT DOCUMENTS

| | | |
|---|---|---|
| WO | WO 99/46356 | 9/1999 |
| WO | WO 00/61086 | 10/2000 |

* cited by examiner

Primary Examiner — Kortney L. Klinkel
Assistant Examiner — Lisbeth C Robinson
(74) Attorney, Agent, or Firm — Servilla Whitney LLC

(57) ABSTRACT

The invention is drawn to fluid concentrate formulations of fatty acid monoethanolamides comprising (a) about 71-76% by weight of one or more C8-C22 fatty acid monoethanolamides, (b) about 15-17% by weight of water, and (c) about 10-12% by weight of one or more hydrotropes, based on the fluid formulation, wherein the fluid formulation is homogeneous, pumpable and color stable at a temperature of less than 55° C. A preferred embodiment is drawn to fluid concentrate formulations of cocamide monoethanolamide (CMEA) consisting of (a) about 71-76% by weight of CMEA, (b) about 15-17% by weight of water, and (c) about 10-12% by weight of glycerol, based on the fluid formulation. Methods of preparing the fluid concentrate formulations mulations are also disclosed. The fluid concentrate formulations of fatty acid monoethanolamides are useful in the preparation of cosmetic and pharmaceutical compositions.

4 Claims, 2 Drawing Sheets

FLUID COCAMIDE MONOETHANOLAMIDE CONCENTRATES AND METHODS OF PREPARATION

CROSS-REFERENCE TO RELATED APPLICATIONS

This application is the national stage entry of PCT/EP2011/000948, filed on Feb. 26, 2011, which claims priority to U.S. Provisional Application No. 61/313,395, filed on Mar. 12, 2010, the disclosures of which are incorporated herein by reference in their entireties.

FIELD OF THE INVENTION

The invention is directed to the preparation of fluid concentrate formulations of the nonionic surfactants fatty acid monoethanolamides, particularly cocamide monoethanolamide (CMEA), having improved handling and stability properties, for use in cosmetic and pharmaceutical compositions.

BACKGROUND OF THE INVENTION

Fatty acid monoethanolamides are useful as components of cosmetic and pharmaceutical preparations, functioning as nonionic surfactants, emulsifiers and/or general adjuvants. Cocamide monoethanolamide (CMEA) is a particularly useful compound in this regard. CMEA is a solid. One commercial solid formulation of CMEA, COMPERLAN® CMEA, available from Cognis Corporation, is 89% CMEA and 11% glycerol, with a melting range of about 62-66° C. Fatty acid monoethanolamide products, in particular CMEA products, are typically supplied as pellets or flakes. However, it would be desirable to handle the product as a fluid concentrate to facilitate transfer during transit and production. Such fluid formulations would offer cost savings in terms of lower manufacturing, packaging, transportation and storage costs. However, COMPERLAN® CMEA maintained at 65° C. in its molten state rapidly darkens in color to an unacceptable level for personal care or pharmaceutical products (Gardner color index>11). Thus, concentrate formulations of CMEA which are stable and fluid at relatively low temperatures would be desirable, in order to conserve energy in handling, transport and storage. Such formulations must also have low viscosity and be pumpable in order to facilitate manufacturing and transport operations.

Surprisingly, it has now been discovered that fluid concentrate formulations of fatty acid monoethanolamides, specifically fluid concentrate formulations of CMEA, which contain a specific and narrow range of water and glycerol, meet these criteria.

BRIEF SUMMARY OF THE INVENTION

Addition of specific amounts of water and hydrotropes to fatty acid monoethanolamides provides concentrates which are fluid at a temperature of less than 55° C., particularly at about 50° C., and further demonstrate the desired stability and physical properties. Specifically, addition of water and glycerol to CMEA provides concentrates with the desired characteristics.

One embodiment of the invention is a fluid fatty acid monoethanolamide concentrate formulation comprising:
 (a) about 71-76% by weight of one or more fatty acid monoethanolamides,
 (b) about 15-17% by weight of water, and
 (c) about 10-12% by weight of a hydrotrope, preferably glycerol, all weight percents being based on the fluid formulation,
wherein the fluid formulation is homogeneous, pumpable and color stable at a temperature of less than 55° C., particularly at about 50° C.

A preferred embodiment is a fluid CMEA concentrate formulation consisting of components (a), (b) and (c) only. A particularly preferred embodiment consists of about 74% CMEA, about 16% water and about 10% glycerol by weight.

Another embodiment of the invention is a method of preparing a fluid formulation of fatty acid monoethanolamides comprising:
 (a) providing a mixture consisting essentially of one or more fatty acid monoethanolamides and glycerol,
 (b) adding water,
 (c) optionally, adding additional hydrotrope, preferably glycerol, and
 (d) mixing with heating to at least a temperature of 50° C., wherein said fluid formulation is homogeneous, pumpable and color stable at a temperature of less than 55° C., particularly at about 50° C.

A preferred embodiment is a method consisting of steps (a) through (d) only. Preferably, the mixture (a) consists of about 89% CMEA and about 11% glycerol.

Yet another embodiment of the invention is a method of preparing a fluid formulation of fatty acid monoethanolamides, comprising:
 (a) providing an amount of one or more fatty acid monoethanolamides,
 (b) adding about 15-17% by weight of water and about 10-12% by weight of hydrotrope, preferably glycerol, based on the fluid formulation, and
 (c) mixing with heating to a temperature of at least 50° C., wherein said fluid formulation is homogeneous, pumpable and color stable at a temperature of less than 55° C., particularly at about 50° C.

A preferred embodiment is a method consisting of components (a), (b) and (c) only. A particularly preferred embodiment is the method consisting of about 74% CMEA, about 16% water and about 10% glycerol by weight.

The fluid concentrate formulations of the invention are pumpable, having a Brookfield viscosity of about 50000 cps or less at 50° C., preferably about 18000 cps or less at 50° C.

DETAILED DESCRIPTION OF PREFERRED EMBODIMENTS

Figure 1:
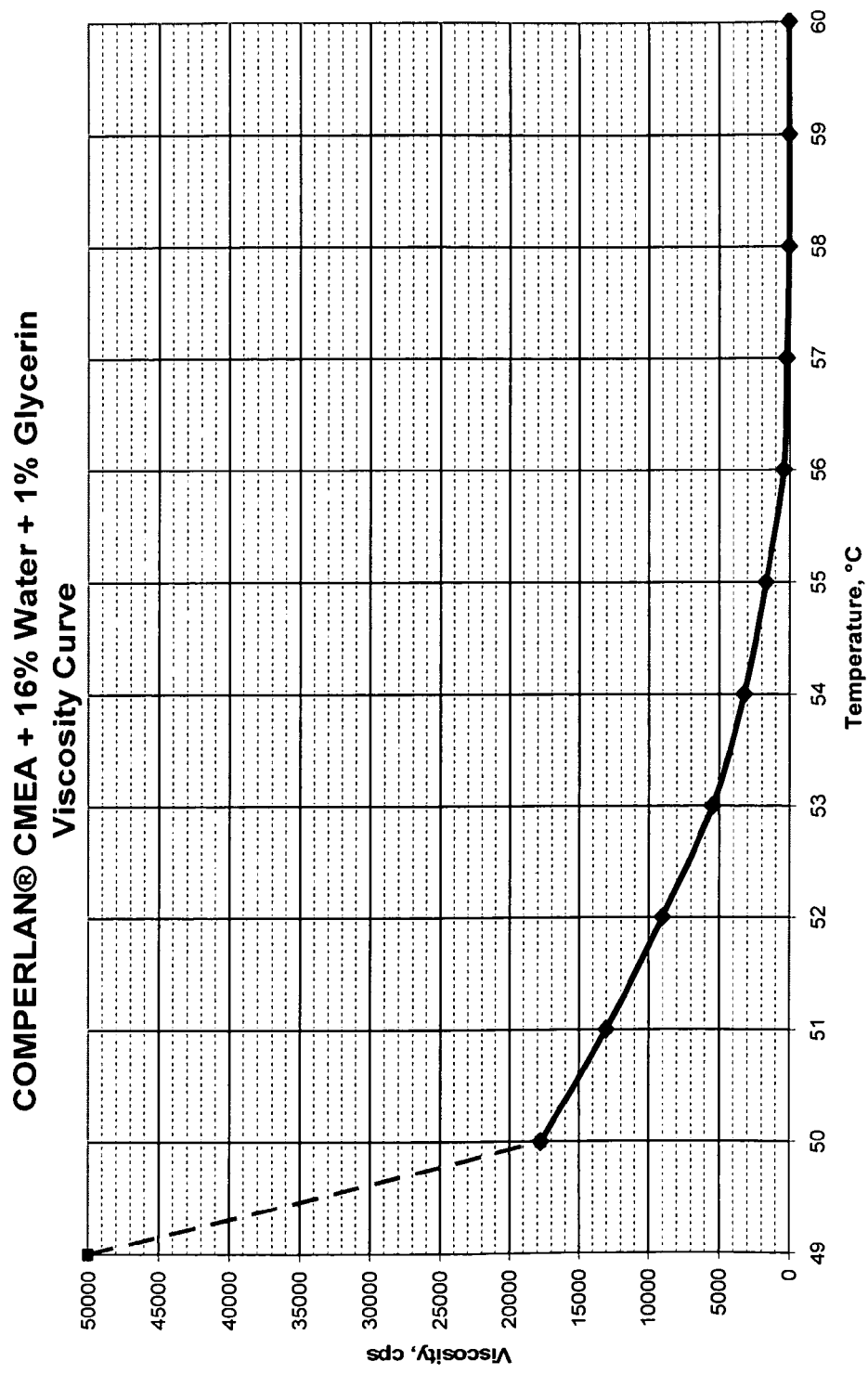
FIG. 1 shows the viscosity curve of a preferred embodiment of the invention consisting of 83% COMPERLAN® CMEA, 16% water and 1% additional glycerol.

We have discovered that homogeneous, flowable and pumpable fluid concentrate formulations of fatty acid monoethanolamides, which are stable with regard to separation and darkening when kept at their fluid temperature, can be prepared by adding water and a hydrotrope, within narrow concentration ranges, to the fatty acid monoethanolamide. These fluid concentrate formulations constitute an advantageous means for storing, distributing, processing, and generally manipulating these nonionic surfactants, thereby simplifying manufacturing operations and reducing costs. A particularly preferred product is the fluid concentrate formulation of CMEA.

For the purposes of the present application, the term "fluid" may also mean "liquid" or "molten" at the specified temperature or temperature range. The term "pumpable" is defined as is commonly understood in normal manufacturing operations in a home and/or personal care production plant.

Fluid Concentrate Formulations of Fatty Acid Monoethanolamides

One embodiment of the invention is directed to fluid concentrate formulations of fatty acid monoethanolamides, comprising:
(a) about 71-76% by weight, based on the fluid formulation, of one or more fatty acid monoethanolamides,
(b) about 15-17% by weight of water, based on the fluid formulation, and
(c) about 10-12% by weight, based on the fluid formulation, of one or more hydrotropes,
wherein said fluid formulation is homogeneous, pumpable and color stable at a temperature of less than 55° C., particularly at about 50° C.

Monoethanolamides of C8-C22 fatty acids are preferred as component (a). The fatty acid moieties may be saturated or unsaturated, branched or linear, and may be mixtures, such as those derived from natural sources. A particularly preferred fatty acid mixture is coconut fatty acid.

Hydrotropes are well-known adjuvants in the cosmetic and pharmaceutical formulation arts. For the purposes of the present invention, the hydrotropes of component (c), without limitation, may be selected from glycerol, propylene glycol, diethyleneglycol, triethyleneglycol, ethanol, isopropanol, and combinations thereof. A particularly preferred hydrotrope is glycerol.

The fluid fatty acid monoethanolamide formulations may further comprise one or more cosmetic and/or pharmaceutical components. Such components may include, without limitation, oil components, other surfactants, preservatives, antioxidants, thickeners, viscosity regulators, and perfumes.

Another embodiment of the invention is directed to methods of preparing fluid formulations of fatty acid monoethanolamides. A first method of preparing a fluid concentrate formulation of fatty acid monoethanolamides comprises:
(a) providing a mixture consisting essentially of one or more fatty acid monoethanolamides and glycerol,
(b) adding water,
(c) optionally, adding additional hydrotrope, and
(d) mixing with heating to at least a temperature of 50° C., wherein said fluid formulation is homogeneous, pumpable and color stable at a temperature of less than 55° C., preferably at about 50° C.

The additional hydrotrope (c) may comprise glycerol, as is already present in component (a), or a different hydrotrope. Preferably the additional hydrotrope (c) comprises glycerol.

Monoethanolamides of C8-C22 fatty acids are preferred as component (a). The fatty acid moieties may be saturated or unsaturated, branched or linear, and may be mixtures, such as those derived from natural sources. Preferably, the fatty acid monoethanolamide component of mixture (a) comprises cocamide monoethanolamide, in about 89% by weight based on the mixture of fatty acid monoethanolamide and glycerol. Preferably this mixture is present in about 80-85%, most preferably about 83% by weight, based on the fluid formulation. Preferably the fluid formulation comprises water in about 15-17%, most preferably about 16% by weight, and additional glycerol in about 1-3%, most preferably about 1% by weight, based on the fluid formulation. Based on an 89:11 mixture of CMEA and glycerol, these percentages are equivalent to about 71-76%, most preferably about 74%, of fatty acid monoethanolamide, and about 10-12%, most preferably about 10%, of glycerol, based on the fluid formulation.

A second method of preparing a fluid formulation of fatty acid monoethanolamides comprises:
(a) providing an amount of one or more fatty acid monoethanolamides,
(b) adding about 15-17%, preferably about 16%, by weight of water and about 10-12%, preferably about 10% by weight of hydrotrope, based on the fluid formulation, and
(c) mixing with heating to a temperature of at least 50° C., wherein said fluid formulation is homogeneous, pumpable and color stable at a temperature of less than 55° C., preferably about 50° C.

The fluid concentrate formulations of the invention are pumpable, having a Brookfield viscosity of about 50000 cps or less at 50° C., preferably about 18000 cps or less at 50° C.

Preferably the hydrotrope comprises glycerol. Monoethanolamides of C8-C22 fatty acids are preferred as component (a). The fatty acid moieties may be saturated or unsaturated, branched or linear, and may be mixtures, such as those derived from natural sources. A particularly preferred fatty acid mixture is coconut fatty acid.

Fluid Concentrate Formulations of Cocamide Monoethanolamide (CMEA)

Cocamide monoethanolamide (CMEA) is preferred as the fatty acid monoethanolamide. A particularly preferred source of CMEA is COMPERLAN® CMEA, which is 89% CMEA and 11% glycerol, available from Cognis Corporation. By the addition of 15-17% of water to COMPERLAN® CMEA, the initial melting range can be reduced to about 50° C. The resulting formulation, containing CMEA, water and glycerol, does not darken as much in color while in its fluid state, reaching a maximum Gardner color index of 7 after 6 weeks at 50° C. The further addition of glycerol increases both the color stability at 50° C. as measured by the Gardner color index, as well as the storage stability as evidenced by phase stability over time. Surprisingly, it has been discovered that the compositions that provide the desired combination of
1) appropriate pumpable viscosity for industrial processing and handling operations,
2) homogeneity without phase separation, and
3) acceptable color stability,
all at 50° C., are found uniquely in the following narrow range of components:

| | |
|---|---|
| CMEA | 71-76% (equivalent to 80-85% COMPERLAN ® CMEA) |
| Water | 15-17% |
| Glycerol | 10-12% (1-3% glycerol in addition to COMPERLAN ® CMEA above) |

One embodiment of the invention is directed to fluid formulations of CMEA, comprising:
(a) about 71-76% by weight of cocamide monoethanolamide,
(b) about 15-17% by weight of water, and
(c) about 10-12% by weight of glycerol, based on the fluid formulation, wherein said fluid formulation is homogeneous, pumpable and stable at a temperature of less than 55° C., particularly at about 50° C.

A preferred embodiment of the invention comprises:
(a) about 74% by weight of cocamide monoethanolamide,
(b) about 16% by weight of water, and
(c) about 10% by weight of glycerol, based on the fluid formulation.

The fluid concentrate formulations of the invention are pumpable, having a Brookfield viscosity of about 50000 cps or less at 50° C., preferably about 18000 cps or less at 50° C.

Another embodiment of the invention is directed to methods of preparing fluid formulations of CMEA. A first method of preparing a fluid formulation of cocamide monoethanolamide comprises:
(a) providing a mixture consisting essentially of cocamide monoethanolamide and glycerol,
(b) adding water,
(c) optionally, adding additional glycerol, and
(d) mixing with heating to at least a temperature of 50° C., wherein said fluid formulation is homogeneous, pumpable and stable at a temperature of less than 55° C., particularly at about 50° C.

Preferably the mixture (a) consists of CMEA and glycerol, and is about 89% CMEA and about 11% glycerol, represented by the commercial product COMPERLAN® CMEA. When mixture (a) is present in about 80-85% by weight based on the fluid concentrate formulation, then CMEA is present in the optimum weight range of about 71-76% and glycerol is present in about 9% by weight based on the fluid concentrate formulation. Optionally, further additions of about 1-3% of glycerol may be added to bring the glycerol content into the optimum range of about 10-12% based on the fluid concentrate formulation. Water is added in the optimum range of about 15-17% by weight based on the fluid concentrate formulation. A particularly preferred method comprises providing about 83% COMPERLAN® CMEA, and adding about 16% water and about 1% additional glycerol, which is equivalent to providing about 74% CMEA, and adding about 16% water and about 10% glycerol by weight, based on the fluid concentrate formulation. Preferably the fluid concentrate formulations of the method have Brookfield viscosities of about 18000 cps or less at 50° C.

A second method of preparing a fluid formulation of cocamide monoethanolamide comprises:
(a) providing an amount of cocamide monoethanolamide,
(b) adding about 15-17% by weight of water and about 10-12% by weight of glycerol, based on the fluid formulation, and
(c) mixing with heating to a temperature of at least 50° C., wherein said fluid formulation is homogeneous, pumpable and stable at a temperature of less than 55° C., particularly at about 50° C.

Preferably, the method comprises adding about 16% water and about 10% glycerol by weight, based on the fluid formulation, to CMEA. Preferably the fluid concentrate formulations of the method have Brookfield viscosities of about 18000 cps or less at 50° C.

Particularly preferred embodiments of the invention are those consisting only of the specified components of the fluid formulation, or consisting only of the specified steps of the methods of preparing the fluid formulations.

Thus, one particularly preferred embodiment of the invention is directed to fluid formulations of CMEA consisting of:
(a) about 71-76% by weight of cocamide monoethanolamide,
(b) about 15-17% by weight of water, and
(c) about 10-12% by weight of glycerol, based on the fluid formulation,
wherein said fluid formulation is homogeneous, pumpable and stable at a temperature of less than 55° C., particularly at about 50° C.

A most particularly preferred embodiment of the invention consists of:
(a) about 74% by weight of cocamide monoethanolamide,
(b) about 16% by weight of water, and
(c) about 10% by weight of glycerol, based on the fluid formulation.

Preferably these fluid concentrate formulations have Brookfield viscosities of about 18000 cps or less at 50° C.

A first particularly preferred method of preparing a fluid formulation of cocamide monoethanolamide consists of:
(a) providing a mixture consisting of cocamide monoethanolamide and glycerol,
(b) adding water,
(c) optionally, adding additional glycerol, and
(d) mixing with heating to at least a temperature of 50° C., wherein said fluid formulation is homogeneous, pumpable and stable at a temperature of less than 55° C., particularly at about 50° C.

Preferably the mixture (a) consisting of CMEA and glycerol, is about 89% CMEA and about 11% glycerol, represented by the commercial product COMPERLAN® CMEA. When mixture (a) is present in about 80-85% by weight based on the fluid concentrate formulation, then CMEA is present in the optimum weight range of about 71-76%, and glycerol is present in about 9% by weight based on the fluid concentrate formulation. Optionally, further additions of about 1-3% of glycerol may be added to bring the glycerol content into the optimum range of about 10-12% based on the fluid concentrate formulation. Water is added in the optimum range of about 15-17% by weight based on the fluid concentrate formulation. A most particularly preferred method consists of providing about 83% COMPERLAN® CMEA, and adding about 16% water and about 1% additional glycerol, which corresponds to providing about 74% CMEA, and adding about 16% water and about 10% glycerol by weight, based on the fluid concentrate formulation. Preferably the fluid concentrate formulations of the method have Brookfield viscosities of about 18000 cps or less at 50° C.

A second particularly preferred method of preparing a fluid formulation of cocamide monoethanolamide, consists of:
(a) providing an amount of cocamide monoethanolamide,
(b) adding about 15-17% by weight of water and about 10-12% by weight of glycerol, based on the fluid formulation, and
(c) mixing with heating to a temperature of at least 50° C., wherein said fluid formulation is homogeneous, pumpable and stable at a temperature of less than 55° C., particularly at about 50° C. Preferably, the method consists of adding about 16% water and about 10% glycerol by weight, based on the fluid formulation, to CMEA. Preferably the fluid concentrate formulations of the method have Brookfield viscosities of about 18000 cps or less at 50° C.

EXAMPLES

Figure 2:
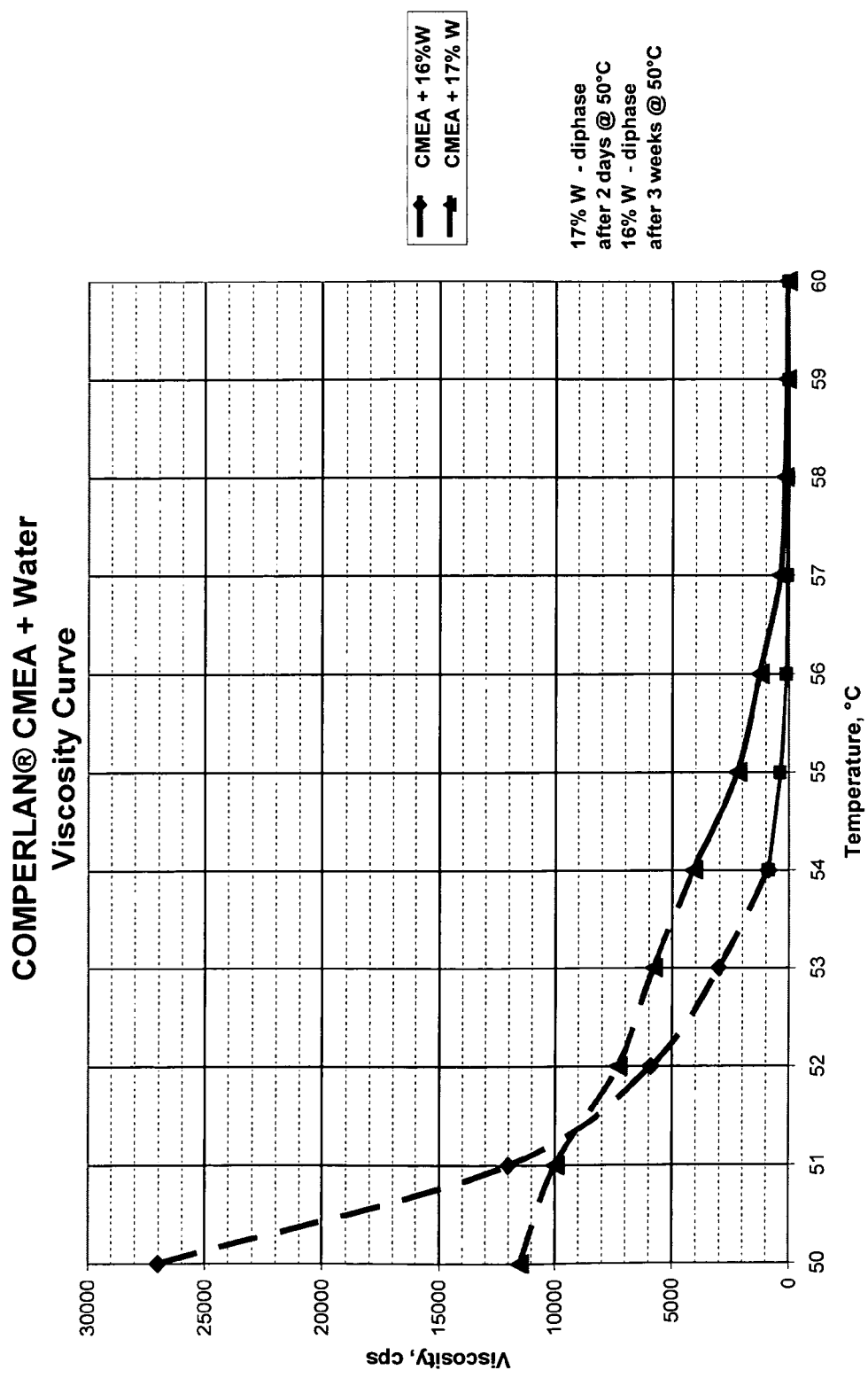
FIG. 2 shows the viscosity curves of two preferred embodiments of the invention consisting of COMPERLAN® CMEA and either 16% water or 17% water.

As shown in Table 1, the desired stability and viscosity properties of the fluid CMEA formulations are attained only within the narrow percentage ranges of components disclosed above. Thus, fluid concentrate formulations consisting of COMPERLAN® CMEA and 15-20% water (without added glycerol) showed the desired phase stability only for the 15% water formulation (Example 1). Addition of further glycerol at 1-3% improved the phase stability, with the combination of 1% additional glycerol and 16% water (Example 5) showing a desirable combination both of phase stability and low viscosity. FIGS. 1 and 2 show the graphs of viscosity versus temperature for Example 5 (FIG. 1) and Examples 2 and 3 (FIG. 2).

Although the data is not shown, the rank ordering of initial viscosity at 50° C. is: Example 1>Example 6>Example 5.

TABLE 1

Fluid CMEA Formulations and Physical Data

| Example | COMPERLAN® CMEA[1] wt % | Water wt % | Additional glycerol wt % | Initial Brookfield viscosity[2] | Phase stability |
|---|---|---|---|---|---|
| 1 | 85 | 15 | 0 | | stable 6 weeks |
| 2 | 84 | 16 | 0 | 27000 | separated 3 weeks |
| 3 | 83 | 17 | 0 | 11500 | separated 2 days |
| 4 | 80 | 20 | 0 | | separated 1 day |
| 5 | 83 | 16 | 1 | 17750 | stable 6 weeks |
| 6 | 80 | 17 | 3 | | stable 6 weeks |

[1]Cocamide monoethanolamide, 89%; glycerol, 11%.
[2]Cps at 50° C.

Table 2 shows the color stability of Example 5 over the course of 6 weeks at 50° C. This fluid formulation is far superior in color stability compared to COMPERLAN® CMEA held at it's fluid temperature of 65° C.

TABLE 2

Color Stability of Fluid CMEA Formulations Held at Fluid Temperature

| Fluid Formulation | Initial Gardner Color | 1 d | 2 d | 6 d | 1 wk | 2 wk | 3 wk | 4 wk | 6 wk |
|---|---|---|---|---|---|---|---|---|---|
| COMPERLAN® CMEA[1] | 5 | 6 | 6 | 7 | 7 | 7 | 8 | 8 | >11 |
| Example 5[2] | 5 | 5 | 5 | 5 | 5 | 6 | 6 | 7 | 7 |

[1]Cocamide monoethanolamide, 89%; glycerol, 11%; held at 65° C.
[2]Held at 50° C.

A desirable balance of viscosity, phase stability and color stability, all at 50° C., is embodied in Example 5. Therefore, a most particularly preferred composition of the invention consists of 83% COMPERLAN® CMEA, 16% water and 1% additional glycerol, based on the fluid concentrate formulation. This is equivalent to the composition consisting of 74% CMEA, 16% water and 10% glycerol, based on the fluid concentrate formulation.

What is claimed is:

1. A fluid formulation of cocamide monoethanolamide, comprising, by weight of the fluid formulation:
    (a) about 74% of the cocamide monoethanolamide,
    (b) about 16% of water, and
    (c) about 10% of glycerol,
wherein said fluid formulation is homogeneous, pumpable, and color stable at a temperature of less than 55° C.

2. The fluid formulation of claim 1, further comprising one or more cosmetic and/or pharmaceutical components.

3. The fluid formulation of claim 2, wherein said cosmetic and/or pharmaceutical components are selected from the group consisting of oil components, other surfactants, preservatives, antioxidants, thickeners, viscosity regulators, and perfumes.

4. The fluid formulation of claim 1 having a Brookfield viscosity of about 50000 cps or less at 50° C.

* * * * *